United States Patent
Ohayon

(10) Patent No.: US 10,182,755 B2
(45) Date of Patent: Jan. 22, 2019

(54) PUPIL DISTORTION MEASUREMENT AND PSYCHIATRIC DIAGNOSIS METHOD

(71) Applicant: Jacques Ohayon, Wayne, NJ (US)

(72) Inventor: Jacques Ohayon, Wayne, NJ (US)

( * ) Notice: Subject to any disclaimer, the term of this patent is extended or adjusted under 35 U.S.C. 154(b) by 0 days.

(21) Appl. No.: 15/853,899

(22) Filed: Dec. 25, 2017

(65) Prior Publication Data

US 2018/0132775 A1    May 17, 2018

Related U.S. Application Data

(60) Provisional application No. 62/443,230, filed on Jan. 6, 2017.

(51) Int. Cl.
| | |
|---|---|
| G06K 9/00 | (2006.01) |
| A61B 5/16 | (2006.01) |
| G06T 7/90 | (2017.01) |
| G06T 7/00 | (2017.01) |
| G06T 7/73 | (2017.01) |

(52) U.S. Cl.
CPC .............. *A61B 5/163* (2017.08); *A61B 5/165* (2013.01); *G06K 9/0061* (2013.01); *G06K 9/00604* (2013.01); *G06K 9/00617* (2013.01); *G06T 7/0014* (2013.01); *G06T 7/90* (2017.01); *G06T 7/73* (2017.01); *G06T 2207/10024* (2013.01); *G06T 2207/30041* (2013.01); *G06T 2207/30201* (2013.01)

(58) Field of Classification Search
CPC .......................................... G06T 2207/10024
See application file for complete search history.

(56) References Cited

U.S. PATENT DOCUMENTS

| | | |
|---|---|---|
| 3,689,135 A | 9/1972 | Young et al. |
| 3,966,310 A | 6/1976 | Larson |
| 5,646,709 A | 7/1997 | Carter |
| 5,684,562 A | 11/1997 | Fujieda |
| 5,784,145 A | 7/1998 | Ghodse et al. |
| 5,790,235 A | 8/1998 | Kirschbaum |
| 6,637,885 B2 | 10/2003 | Petrali |
| 7,284,858 B2 | 10/2007 | Bergner et al. |
| 7,488,294 B2 | 2/2009 | Torch |

(Continued)

FOREIGN PATENT DOCUMENTS

| | | |
|---|---|---|
| CN | 203263362 U | 11/2013 |
| CN | 203914866 U | 11/2013 |

(Continued)

OTHER PUBLICATIONS

Borza et al. "Real-Time Detection and Measurement of Eye Features from Color images" Sensors, Jul. 16, 2016.*

(Continued)

*Primary Examiner* — Oneal R Mistry

(57) ABSTRACT

A prediction, diagnosis, or suggesting of a diagnosis of a psychiatric disorder is made based in embodiments of the disclosed technology by determining a shape of one or both pupils in an image of a patient. Such a diagnosis can be made in real-time by diagnosing the patient, or by viewing a digitized version of the patient's face as part of post-processing. By finding a pupil which is ovoid or irregular shape (non-circular) and/or comparing the shape to that of shapes of people with known psychiatric disorders, a diagnosis can be suggested.

13 Claims, 4 Drawing Sheets

(56) References Cited

U.S. PATENT DOCUMENTS

| | | | |
|---|---|---|---|
| 7,753,525 B2 | 7/2010 | Hara et al. | |
| 7,798,643 B2 | 9/2010 | Waldorf et al. | |
| 8,323,216 B2 | 12/2012 | Fabian | |
| 9,125,559 B2 | 9/2015 | Kersting et al. | |
| 9,265,458 B2 | 2/2016 | Stack | |
| 9,301,678 B2 | 4/2016 | Hirsh | |
| 9,357,966 B1* | 6/2016 | Cohen | A61B 3/113 |
| 2007/0116380 A1* | 5/2007 | Ciuc | G06T 5/005 |
| | | | 382/275 |
| 2009/0252382 A1* | 10/2009 | Liu | G06K 9/0061 |
| | | | 382/117 |
| 2010/0045933 A1* | 2/2010 | Eberl | A61B 3/113 |
| | | | 351/210 |
| 2014/0064575 A1* | 3/2014 | Flom | G06K 9/00617 |
| | | | 382/116 |
| 2016/0026246 A1* | 1/2016 | Strupczewski | G06T 17/10 |
| | | | 345/420 |
| 2016/0132726 A1 | 5/2016 | Kempinski et al. | |

FOREIGN PATENT DOCUMENTS

| | | |
|---|---|---|
| CN | 103800074 A | 5/2014 |
| CN | 204363951 U | 6/2015 |
| CN | 105078403 B | 9/2016 |
| EP | 2417901 | 2/2012 |
| WO | WO2015164419 | 10/2015 |

OTHER PUBLICATIONS

Dubey (NPL: Iris Localization using Daugman's Intero-Differential Operator International Journal of Computer Applications (0975-8887) (Year: 2014).*

Keeping an Eye on the Ball: Visual Problems on SSRIs, blog,https://rxisk.org/keeping-an-eye-on-the-ball-visual-problems-on-ssris/, accessed Jan. 9, 2018, 4 pages.

* cited by examiner

PUPIL DISTORTION MEASUREMENT AND PSYCHIATRIC DIAGNOSIS METHOD

BACKGROUND

The problem of mass killing, perpetuated by individual shooters, is at epidemic proportions. In recent years, hundreds of innocent individuals have met a violent death from Aurora, Colo. to a Mosque shooting in Quebec City. In addition, the situation appears to be escalating to pilot suicide in the case of the downing of Malaysian flight 370 in March 2014 and the deliberate crashing of German Wings flight 9525 into the Alps March 2015. Since August 2016 until the date of filing of this application, there have been five bus driver suicides that seem to fit the mass killers profile, one in Newark, N.J., one in Chattanooga, Tenn., one in Palm Springs, Calif., one in Baltimore, Md. and one on Sep. 17, 2017 in Queens, N.Y. Of the five, four of the drivers died and many passengers were killed or injured due to the deliberate actions of the drivers. Two recent devastating motor vehicular homicides (one in Uvalde, Tex. in March 2017 and one in Charlottesville, Va. August 2017) also exhibited features that appear to fit profiles of intentional killing.

The common denominator appears to be depression. The diagnosis of depression can be presumed when local police and press reports indicate that anti-depressant medications were prescribed to the perpetrators. It's not uncommon for the medications to be listed in press reports.

What is needed is a way to screen vehicular drivers, pilots, health care professionals, and others for signs of depression or psychiatric disorders. Doing so should prevent many more deaths in the future.

SUMMARY OF THE DISCLOSED TECHNOLOGY

A prediction, diagnosis, or suggesting of a diagnosis of a psychiatric disorder are made based in embodiments of the disclosed technology by determining a shape of one or both pupils in an image of a patient. Such a diagnosis can be made in real-time by diagnosing the patient, or by viewing a digitized version of the patient's face as part of post-processing.

In one embodiment, one creates or receives a digital version of a face of a patient, determines a relative position of facial features of the face of the patient including at least a pupil and iris of at least one eye, and then creates an ovoid shape (a shape based on a perfect circle or oval) representative of the pupil. The shape created follows as close a path as possible to a color or intensity change line between each pupil and each iris. A number of pixels which deviate from a perfect circle and/or perfect oval can also be determined, and this deviation can be used as part of the determination made. Then, based on the determination of the pupil position and its shape difference from that of a perfectly oval and/or circle shape, and/or the eccentricity of the oval, a comparison to previous images of people who are known to have certain psychiatric disorders is made. Based on this comparison, if indicated, a suggested psychiatric disorder for the patient is made.

If the ovoid shape is a perfect circle, in embodiments of the disclosed technology, then a psychiatric disorder is unindicated. Before the step of comparing, the ovoid shape is smoothed to be closer to a true oval and the smoothed version of said ovoid shape is compared in some embodiments of the disclosed technology. A circle is manually overlaid (meaning that input from a user is received indicating where to place the circle and of what size the circle should be) around edges of the pupil in some embodiments. The circle, in such embodiments can be adjusted to become the ovoid shape and capture there-within pixels determined to be represented by the pupil.

An amount of pixels different between the circle and the ovoid shape can be used to determine the suggested psychiatric disorder. An input can be received indicating whether, from said subjective viewpoint of a human, the pupil in the digital version of said face is abnormal, and based on this input, during the step of comparing, the subjective viewpoint is used to determine if the ovoid shape represents a known psychiatric disorder. This subjective viewpoint is made, in embodiments of the disclosed technology, by comparing the pupil of the digital version of the face to a plurality of different circles, each such different circle offset at a different angle to another and representative of a healthy patient.

The prior images and known psychiatric disorders which can be used for a sake of comparison are, in embodiments of the disclosed technology, partially culled from publicly available images of people who have committed violent crimes. Known psychiatric disorders as related to specific shapes of pupils, in some embodiments, are determined based on images of people with non-circular pupils who take or have taken anti-depressant medication.

An indication of/or a selection of a brightest region of the pupil of at least one eye can be provided as an input. This input is then used to determine a threshold of the color or the intensity change in locating the pupil of the at least one eye. The suggested psychiatric disorder can be further suggested based on receiving medical history of the patient and determining that said medication history includes prescription selective serotonin re-uptake inhibitors. One can also magnify the image of the face and/or eye such that the ovoid shape is accurate to a pixel level of detail before determining where a circle or ovoid shape is laid there-over.

Described another way, methods of the disclosed technology include creating or receiving a digital version of a face of a patient, determining a relative position of facial features of the face of the patient including at least a pupil and iris of at least one eye, based on at least the position of the pupil within the face and its brightness (or lack thereof) compared to other parts of the face. A degree in which the at least one pupil is off from being a perfect circle is determined and a suggestion or proposed diagnosis of a psychiatric disorder based on the degree in which said at least one pupil is off from being a perfect circle is used to output a suggestion of a diagnosis or warn of a possible psychiatric condition.

Any device or step to a method described in this disclosure can comprise or consist of that which it is a part of, or the parts which make up the device or step. The term "and/or" is inclusive of the items which it joins linguistically and each item by itself.

DETAILED DESCRIPTION OF EMBODIMENTS OF THE DISCLOSED TECHNOLOGY

A prediction, diagnosis, or suggesting of a diagnosis of a psychiatric disorder are made based in embodiments of the disclosed technology by determining a shape of one or both pupils in an image of a patient. Such a diagnosis can be made in real-time by diagnosing the patient, or by viewing a digitized version of the patient's face as part of post-processing. By finding a pupil which is ovoid or irregular shape (non-circular) and/or comparing the shape to that of shapes of people with known psychiatric disorders, a diagnosis can be suggested.

Embodiments of the disclosed technology are described below, with reference to the figures provided.

Figure 1:
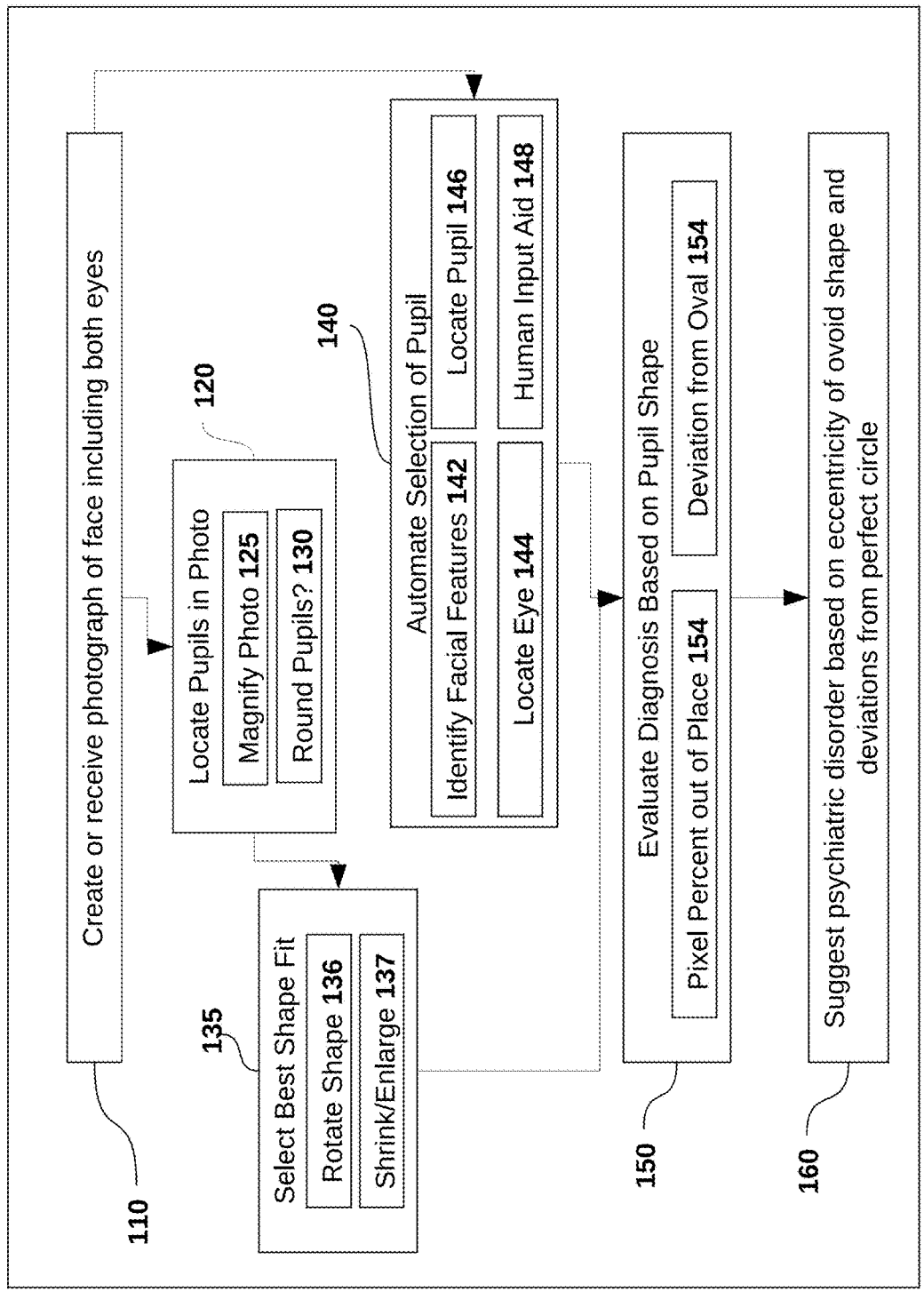
FIG. 1 is a flow chart of a method of carrying out embodiments of the disclosed technology.

FIG. 1 is a flow chart of a method of carrying out embodiments of the disclosed technology. A high pixel rate photo (greater than 5 megapixels) of both patient eyes and face, in step 110, are taken in embodiments of the disclosed technology. Such a photo can then be reviewed by evaluator, such as a law enforcement or health care professional in step 120. In sub-step 125, the photo can be magnified as necessary such as to be able to differentiate each pixel from one another. An input from the evaluator, in step 130 is received indicating whether the pupils of the eye look round. This can be carried out by way of having the evaluator, in sub-step 135 select from various ovoid shapes presented and/or overlaying one of the ovoid shapes over the pupil to make a best fit. Such ovoid shapes can be rotated (step 136) and/or enlarged/shrunk (step 137) to provide the best fit over the iris. It should be understood that the above steps can be carried out for one or both eyes.

Alternatively or in addition, a circle or ovoid shape for placement over the pupil can be determined via an automated process, as shown in step 140. In this step, facial features in the digitized or digital photograph are identified in step 142. More specifically, in step 144, the location of the eye(s) in the picture is determined and in step 146, each iris and pupil is differentiated based on the color. In a color picture, the pupil is black, and the iris is another color such as brown, gray, blue, green, and so on. In a black and white picture, there is a difference in brightness between the black pupil and the non-black iris. Lens flares and reflections may need to be corrected for, and in some cases, a user may be asked, in step 148, to identify the darkest or brightest part of the pupil to confirm that what is detected via the automated selection of the pupil actually is the pupil. It should again be understood that the above steps can be carried out for one or both eyes.

After any of the above or other pathways, the position of the iris is now known, in step 150 and can be evaluated. In step 152, it is determined how many pixels of the pupil/what percentage are deviating from the perfect circle or a perfect oval shape when best drawn in order to evaluate the presence of any distortion in the pupil. A Monte Carlo random number technique can be used to calculate pi and deviation of the pupil from that of a perfect circle and/or perfect oval shape in step 154. In step 160 one can now use the eccentricity of the ovoid shape and deviation of the pupil from that of a perfect circle to determine if the shape is suggestive of a psychiatric disorder which may have been caused by anti-depressants, a serotonin uptake re-inhibitor or the like.

Figure 2:
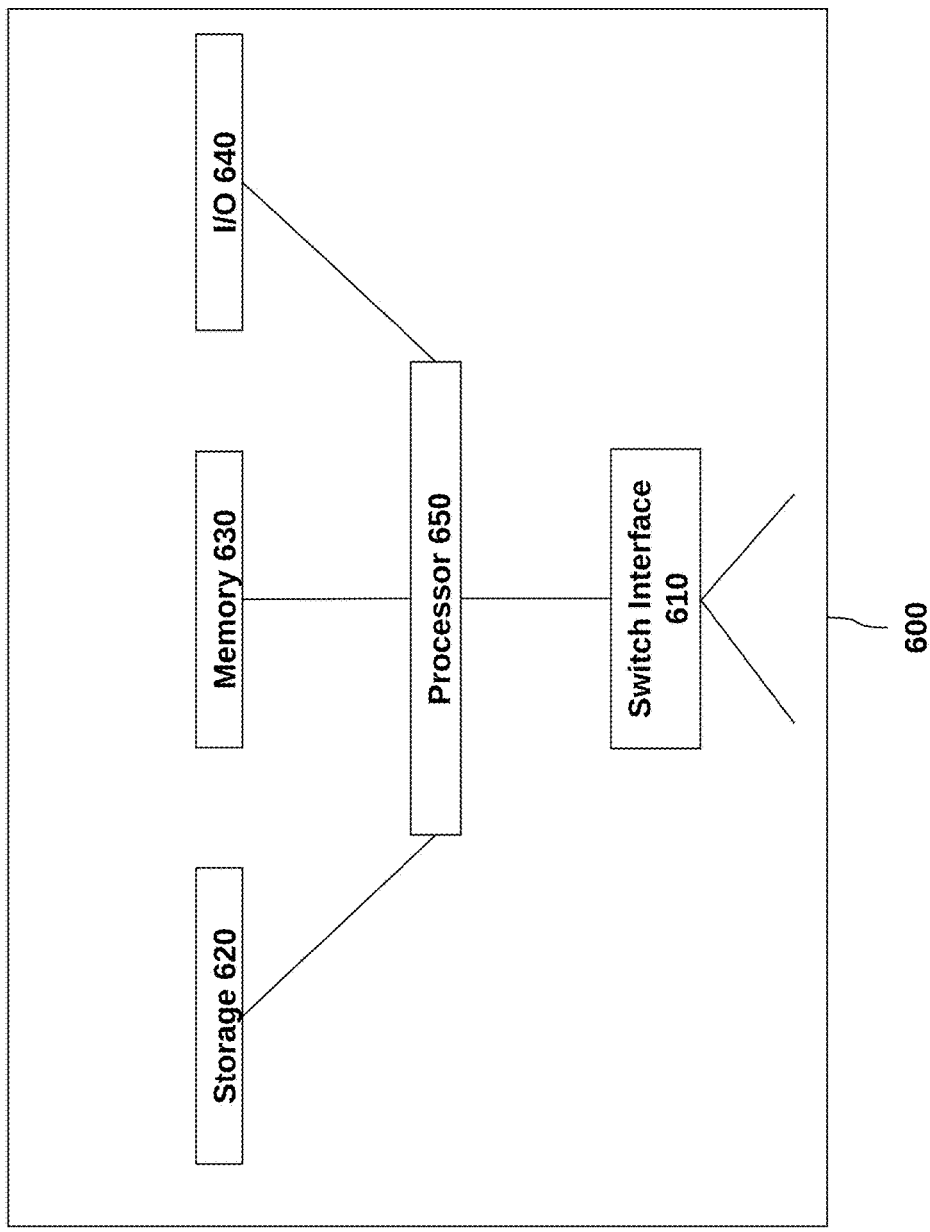
FIG. 2 shows a high-level block diagram of devices used in embodiments of the disclosed technology.

FIG. 2 shows a high-level block diagram of devices used in embodiments of the disclosed technology. Device 600 comprises a processor 650 that controls the overall operation of the computer by executing the device's program instructions which define such operation. The device's program instructions may be stored in a storage device 620 (e.g., magnetic disk, database) and loaded into memory 630 when execution of the console's program instructions is desired. Thus, the device's operation will be defined by the device's program instructions stored in memory 630 and/or storage 620, and the console will be controlled by processor 650 executing the console's program instructions. A device 600 also includes one, or a plurality of, input network interfaces for communicating with other devices via a network (e.g., the internet). The device 600 further includes an electrical input interface. A device 600 also includes one or more output network interfaces 610 for communicating with other devices. Device 600 also includes input/output 640 representing devices, which allow for user interaction with a computer (e.g., display, keyboard, mouse, speakers, buttons, etc.). One skilled in the art will recognize that an implementation of an actual device will contain other components as well, and that FIG. 7 is a high-level representation of some of the components of such a device, for illustrative purposes. It should also be understood by one skilled in the art that the method and devices depicted in FIG. 1 may be implemented on a device such as is shown in FIG. 7.

Further, it should be understood that all subject matter disclosed herein is directed at, and should be read only on, statutory, non-abstract subject matter. All terminology should be read to include only the portions of the definitions which may be claimed. By way of example, "computer readable storage medium" is understood to be defined as only non-transitory storage media.

Figure 3:
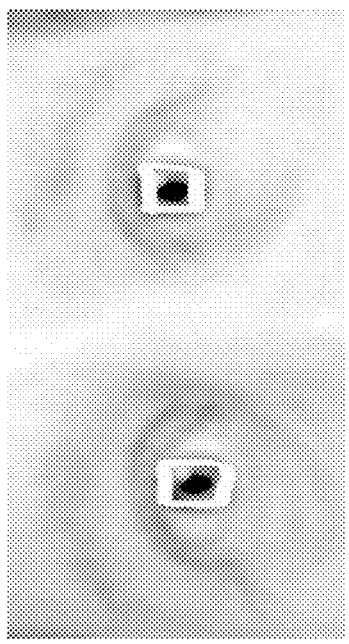
FIG. 3 shows examples of determining locations of pupils by inscribing the eye in a rectangle and using a Monte Carlo method of finding an ovoid shape of the pupil in an embodiment of the disclosed technology.
Figure 3:
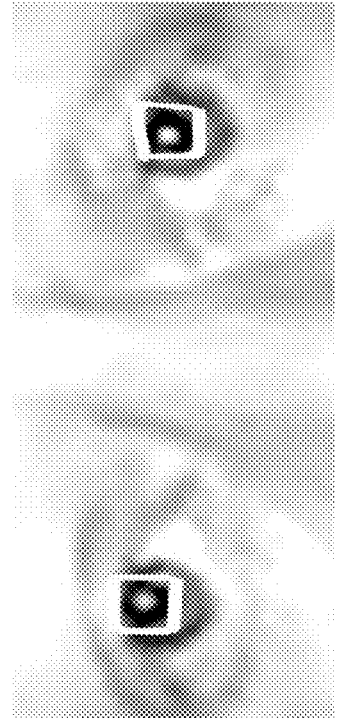
Figure 3:
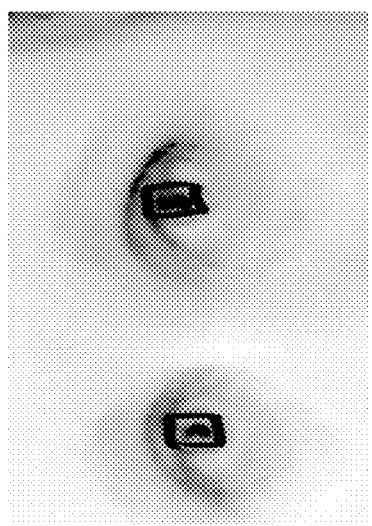
Figure 3:
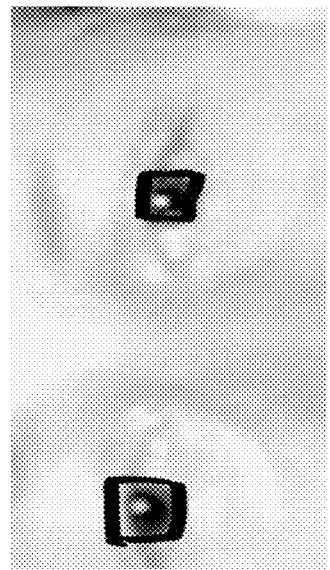

FIG. 3 shows examples of determining locations of pupils by inscribing the eye in a rectangle and using a Monte Carlo method of finding an ovoid shape of the pupil in an embodiment of the disclosed technology. Here, four examples are shown, taking publicly available pictures of Desiree Merrell (baby killer), Kevin Loibl (obsessed murderer), Kevin Neal (shooter/mass murderer), and Stephan Paddock (mass murderer). First, an area of their pupil is determined in each picture based on its intensity or coloration. This can be after converting the picture to black and white so that the pupil stands out further from the background. Then, pixel by pixel a determination is made as to where exactly the pupil is and how close it is to a circular or ovoid shape. The Monte Carlo method of determining the shape of the pupil can be used to find a closest circle or oval/ovoid shape which fits over the pupil based on probability and the law of large numbers. Described more specifically based on the Wikipedia article of the same name, Monte Carlo methods (or Monte Carlo experiments) are defined herein as a broad class of computational algorithms that rely on repeated random sampling to obtain numerical results by using randomness to solve problems that might be deterministic in principle. This is done, in the examples shown in FIG. 3, by drawing a square around the pupil and then inscribing a circle within it. Uniformly scattered objects of uniform size, that is pixels, are placed over the square. The number of objects inside the circle and the total number of objects are juxtaposed to create a ratio of inside-count and the total-sample-count is an estimate of the ratio of the two areas, which is $\pi/4$. Then the size and position of the best circle is determined based on which best approximates the value of $\pi$ and inscribed circle in the rectangle.

In a perfect circle inscribed in a perfect square, Pi/4=0.785784. This corresponds roughly to 78.5% of the square being filled with the pupil if the pupil were a perfect circle. Any deviation from this number could indicate a distortion. A threshold of distortion which might indicate that a medical/psychiatric condition should be suggested is 10% in some embodiments of the disclosed technology. Thus, a result, such as shown in FIG. 3, yielding a number greater than about 86% or less than about 71% would be cause for such a suggestion or diagnosis. In another embodiment, a 20% threshold might be desired, such as for diagnosing a different medical condition. Thus, a result of less than 67% or greater than 90% might warrant such a diagnosis in this embodiment.

Figure 4:
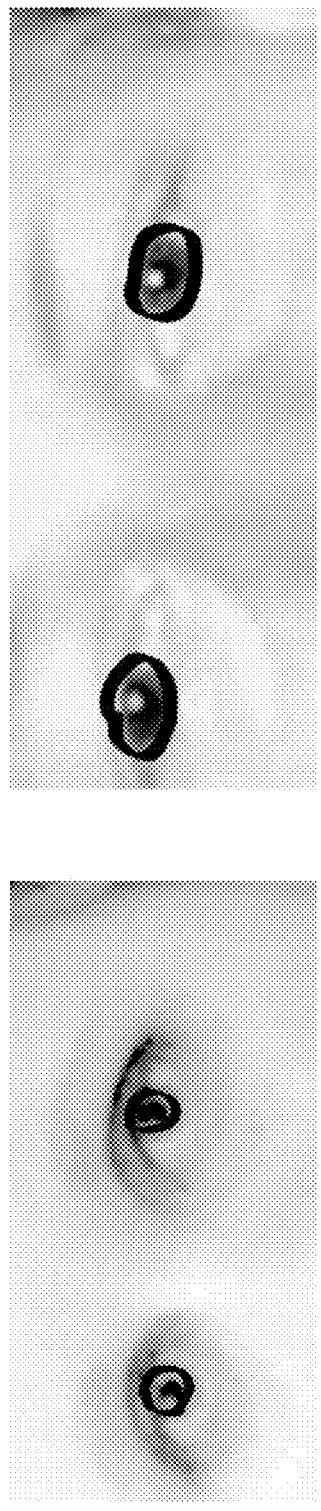
FIG. 4 shows examples of determining locations of pupils by circling the eye and locating the shape of the pupils therein in an embodiment of the disclosed technology.
Figure 4:
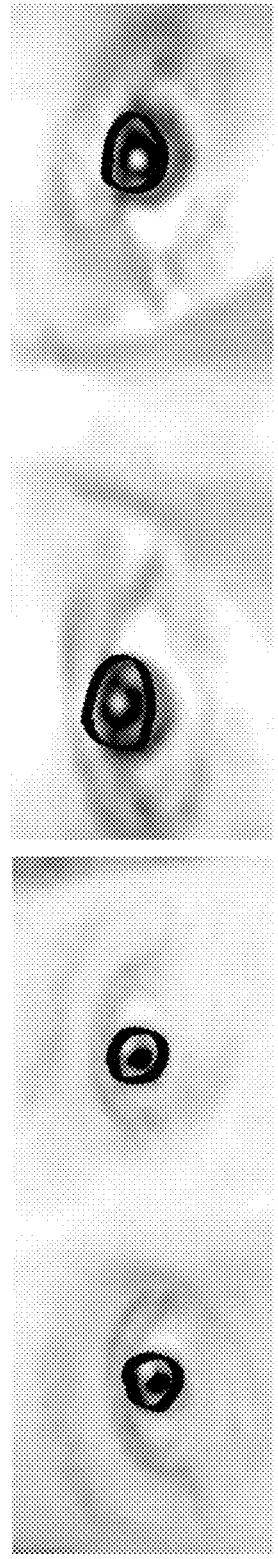

FIG. 4 shows examples of determining locations of pupils by circling the eye and locating the shape of the pupils therein in an embodiment of the disclosed technology. Here, the circle is drawn around the eye based on a user being prompted for same and drawing the circle or a determination being made based on where the pixels change colors after determining the relative location of the eye within a face. A similar method, as described with reference to FIG. 3, is then carried out.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the disclosed technology.

I claim:

1. A method of diagnosing a patient, comprising:
   obtaining, using a high-resolution digital camera comprising greater than 5-megapixel resolution, a digitized representation at a given instant of a face of the patient;
   determining, using a networked processing device, a relative position of a pupil of at least one eye of the patient by using a color or intensity change line between the pupil and an iris associated with the pupil of the patient in the digitized representation;
   creating, using the networked processing device, an ovoid shape, the ovoid shape following as close a path as possible to the color or intensity change line between the pupil and the iris associated with the pupil;
   inscribing, using the networked processing device, the pupil and ovoid shape in a square;
   uniformly, using the networked processing device, scattering pixels over the square, the uniformly scattered pixels being uniformly sized;
   determining, using the networked processing device, a ratio of a quantity of pixels disposed inside the ovoid shape to a quantity of pixels disposed inside the square;
   determining, using the networked processing device, a deviation of the ovoid shape from a circle based on a deviation of the ratio from pi/4; and
   comparing the deviation to a threshold of distortion, and in response to the deviation exceeding the threshold of distortion, outputting a suggestion that the patient is experiencing a medical condition.

2. The method of claim 1, wherein the ovoid shape is a perfect circle, within a pre-defined threshold, the method further comprising: outputting the suggested medical condition.

3. The method of claim 1, further comprising smoothing the ovoid shape to be closer to an oval prior to comparing the smoothed ovoid shape to the shapes of pupils associated with people having known medical condition.

4. The method of claim 3, further comprising:
   overlaying a circle over the pupil; and
   adjusting the circle to become the ovoid shape and capture pixels determined represent the pupil.

5. The method of claim 4, further comprising determining the suggested medical condition based on a difference between a quantity of pixels associated with the circle and a quantity of pixels associated with the ovoid shape.

6. The method of claim 5, further comprising:
   receiving an indication of whether the pupil in the digitized representation of the face is abnormal; and
   during the comparison, using the indication to determine if said ovoid shape represents the known psychiatric disorder.

7. The method of claim 6, further comprising determining the indication by comparing the pupil in the digitized representation of the face to a plurality of different circles, each of the plurality of different circles being offset at a different angle with respect to each other and being representative of a healthy patient.

8. The method of claim 1, further comprising determining the known medical condition to associated with specific shapes of pupils based on images of people who have committed violent crimes.

9. The method of claim 1, further comprising determining the known medical condition associated with specific shapes of pupils based on images of people with non-circular pupils who take anti-depressant medication.

10. The method of claim 7, further comprising:
    receiving an indication of a brightest region of the pupil; and
    determining a threshold of the color or intensity change using the brightest region of the pupil to locate the pupil.

11. The method of claim 1, further comprising determining the suggested medical condition based on medical history of said the patient and medication history comprising a selective serotonin re-uptake inhibitors.

12. The method of claim 4, further comprising, prior to overlaying the circle, magnifying the digitized representation such that the ovoid shape is accurate to a pixel level of resolution.

13. A devise for diagnosing a patient, comprising:
    a high-resolution digital camera comprising greater than 5-megapixel resolution, the high-resolution digital camera obtaining providing a digitized representation at a given instant of a face of the patient; and
    a networked processing device, the networked processing device determining a relative position of a pupil of at least one eye of the patient by using a color or intensity change line between the pupil and an iris associated with the pupil of the patient in the digitized representation, the networked processing device creating an ovoid shape,
    the ovoid shape following as close a path as possible to the color or intensity change line between the pupil and the iris associated with the pupil, the networked processing device inscribing, using the networked processing device, the pupil and ovoid shape in a square;

the networked processing device uniformly, using the networked processing device, scattering pixels over the square, the uniformly scattered pixels being uniformly sized;

the networked processing device determining, using the networked processing device, a ratio of a quantity of pixels disposed inside the ovoid shape to a quantity of pixels disposed inside the square;

the networked processing device determining, using the networked processing device, a deviation of the ovoid shape from a circle based on a deviation of the ratio from pi/4; and the networked processing device comparing the deviation to a threshold of distortion, and in response to the deviation exceeding the threshold of distortion, outputting a suggestion that the patient is experiencing a medical condition.

* * * * *